United States Patent
Kumar KN et al.

(10) Patent No.: US 11,105,787 B2
(45) Date of Patent: Aug. 31, 2021

(54) SYSTEM AND METHOD TO OPTIMIZE CRUDE OIL DISTILLATION OR OTHER PROCESSING BY INLINE ANALYSIS OF CRUDE OIL PROPERTIES

(71) Applicant: Honeywell International Inc., Morris Plains, NJ (US)

(72) Inventors: Dinesh Kumar KN, Bangalore (IN); Soumendra Mohan Banerjee, Dwarka (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 301 days.

(21) Appl. No.: 16/140,770

(22) Filed: Sep. 25, 2018

(65) Prior Publication Data

US 2019/0120810 A1   Apr. 25, 2019

Related U.S. Application Data

(60) Provisional application No. 62/575,171, filed on Oct. 20, 2017.

(51) Int. Cl.
   *G01N 33/28*   (2006.01)
   *C10G 7/12*   (2006.01)
   (Continued)

(52) U.S. Cl.
   CPC .............. *G01N 33/28* (2013.01); *C10G 7/12* (2013.01); *C10G 45/72* (2013.01); *C10G 47/36* (2013.01);
   (Continued)

(58) Field of Classification Search
   CPC .............. G01N 33/28; G01N 33/2823; G05B 23/0294; G06N 20/00
   See application file for complete search history.

(56) References Cited

U.S. PATENT DOCUMENTS

| 4,159,239 A | 6/1979 | Schwartz | 208/113 |
|---|---|---|---|
| 4,267,458 A | 5/1981 | Uram | 290/40 R |

(Continued)

FOREIGN PATENT DOCUMENTS

| EP | 0181744 A1 | 5/1986 | B65G 53/66 |
|---|---|---|---|
| EP | 2746884 A1 | 6/2014 | G05B 23/02 |

(Continued)

OTHER PUBLICATIONS

Basak et al., On-Line Optimization of a Crude Distillation Unit with Constraints on Product Properties, 2002, Ind. Eng. Chem.Res. 2002, 41, pp. 1557-1568 (Year: 2002).*

(Continued)

*Primary Examiner* — Toan M Le

(57) ABSTRACT

An apparatus includes at least one processor configured to obtain inline measurements of one or more properties of crude oil, translate the measurements into a set of process and control parameters, and apply the process and control parameters to process equipment. The process and control parameters configure the process equipment to process the crude oil having the one or more properties. The one or more properties of the crude oil may include at least one of: density, specific gravity, viscosity, carbon residue, and sulfur content of the crude oil. The process and control parameters could be applied to one or more controllers associated with a blending unit in a refinery or to one or more controllers associated with a crude oil distillation column in the refinery.

17 Claims, 5 Drawing Sheets

(51) Int. Cl.
*C10G 45/72* (2006.01)
*C10G 47/36* (2006.01)
*C10G 49/26* (2006.01)
*G06N 20/00* (2019.01)

(52) U.S. Cl.
CPC ......... *C10G 49/26* (2013.01); *G01N 33/2823* (2013.01); *G06N 20/00* (2019.01)

(56) References Cited

U.S. PATENT DOCUMENTS

| | | | |
|---|---|---|---|
| 4,284,494 A | 8/1981 | Bartholic | 208/164 |
| 4,362,614 A | 12/1982 | Asdigian | 208/235 |
| 4,380,146 A | 4/1983 | Yannone | 60/39.281 |
| 4,385,985 A | 5/1983 | Gross | 208/113 |
| 4,411,773 A | 10/1983 | Gross | 208/159 |
| 4,709,546 A | 12/1987 | Weiler | 415/116 |
| 4,775,460 A | 10/1988 | Reno | |
| 4,795,545 A | 1/1989 | Schmidt | |
| 4,902,469 A | 2/1990 | Watson | 376/216 |
| 5,077,252 A | 12/1991 | Owen et al. | 502/43 |
| 5,227,121 A | 7/1993 | Scarola | 340/525 |
| 5,582,684 A | 12/1996 | Holmqvist et al. | 162/49 |
| 5,605,435 A | 2/1997 | Haugen | 137/514 |
| 5,616,214 A | 4/1997 | Leclerc | 162/49 |
| 5,642,296 A | 6/1997 | Saxena | 216/84 |
| 5,666,297 A | 9/1997 | Britt et al. | 364/578 |
| 5,817,517 A | 10/1998 | Perry et al. | 436/55 |
| 6,038,540 A | 3/2000 | Krist et al. | 705/8 |
| 6,081,230 A | 6/2000 | Hoshino | 342/357.32 |
| 6,230,486 B1 | 5/2001 | Yasui | 123/674 |
| 6,266,605 B1 | 7/2001 | Yasui | 60/276 |
| 6,271,845 B1 | 8/2001 | Richardson | 715/764 |
| 6,392,114 B1 | 5/2002 | Shields et al. | 582/719 |
| 6,540,797 B1 † | 4/2003 | Scott | |
| 6,760,716 B1 | 7/2004 | Ganesamoorthi et al. | 706/21 |
| 6,772,044 B1 | 8/2004 | Mathur et al. | 700/204 |
| 6,795,798 B2 | 9/2004 | Eryurek et al. | 702/188 |
| 6,982,032 B2 | 1/2006 | Shaffer et al. | 210/101 |
| 6,983,227 B1 | 1/2006 | Thalhammer-Reyero | |
| 7,006,889 B2 | 2/2006 | Mathur et al. | 700/204 |
| 7,067,333 B1 | 6/2006 | Pasadyn et al. | 438/5 |
| 7,133,807 B2 | 11/2006 | Karasawa | 702/188 |
| 7,151,966 B1 | 12/2006 | Baier et al. | 700/19 |
| 7,246,039 B2 | 7/2007 | Moorhouse | 702/185 |
| 7,313,447 B2 | 12/2007 | Hsuing et al. | 700/9 |
| 7,415,357 B1 | 8/2008 | Stluka et al. | 702/6 |
| 7,567,887 B2 | 7/2009 | Emigholz et al. | 702/182 |
| 7,742,833 B1 | 6/2010 | Herbst et al. | 700/108 |
| 7,836,941 B2 | 11/2010 | Song et al. | |
| 7,877,596 B2 | 1/2011 | Foo Kune et al. | 713/153 |
| 7,925,979 B2 | 4/2011 | Forney et al. | 715/733 |
| 7,936,878 B2 | 5/2011 | Kune et al. | 380/270 |
| 7,979,192 B2 | 7/2011 | Morrison et al. | |
| 7,995,526 B2 | 8/2011 | Liu et al. | 370/329 |
| 8,050,889 B2 | 11/2011 | Fluegge et al. | 702/182 |
| 8,055,371 B2 | 11/2011 | Sanford et al. | 700/108 |
| 8,111,619 B2 | 2/2012 | Liu et al. | 370/229 |
| 8,128,808 B2 | 3/2012 | Hassan et al. | 208/209 |
| 8,204,717 B2 | 6/2012 | McLaughlin et al. | 702/188 |
| 8,244,384 B2 | 8/2012 | Pachner et al. | 700/30 |
| 8,280,057 B2 | 10/2012 | Budampati et al. | 380/270 |
| 8,352,049 B2 | 1/2013 | Hsiung et al. | |
| 8,354,081 B2 | 1/2013 | Wheat et al. | |
| 8,385,436 B2 | 2/2013 | Holm et al. | 375/260 |
| 8,428,067 B2 | 4/2013 | Budampati et al. | 370/395.21 |
| 8,458,778 B2 | 6/2013 | Budampati et al. | 726/6 |
| 8,506,656 B1 † | 8/2013 | Turocy | |
| 8,571,064 B2 | 10/2013 | Kore et al. | 370/469 |
| 8,630,962 B2 | 1/2014 | Maeda | 706/12 |
| 8,644,192 B2 | 2/2014 | Budampati et al. | 370/255 |
| 8,811,231 B2 | 8/2014 | Budampati et al. | 370/255 |
| 8,815,152 B2 | 8/2014 | Burgess et al. | |
| 8,923,882 B2 | 12/2014 | Gandhi et al. | 455/455 |
| 8,926,737 B2 | 1/2015 | Chatterjee et al. | |
| 9,053,260 B2 | 6/2015 | Romatier et al. | |
| 9,134,717 B2 | 9/2015 | Trnka | |
| 9,166,667 B2 | 10/2015 | Thanikachalam | |
| 9,176,498 B2 | 11/2015 | Baramov | |
| 9,354,631 B2 | 5/2016 | Mohideen et al. | |
| 9,571,919 B2 | 2/2017 | Zhang et al. | |
| 9,580,341 B2 | 2/2017 | Brown et al. | C02F 3/006 |
| 9,751,817 B2 | 9/2017 | Jani et al. | |
| 9,864,823 B2 | 1/2018 | Horn et al. | |
| 9,968,899 B1 | 5/2018 | Gellaboina et al. | |
| 10,095,200 B2 | 10/2018 | Horn et al. | |
| 10,107,295 B1 | 10/2018 | Brecheisen | |
| 10,180,680 B2 | 1/2019 | Horn et al. | |
| 10,183,266 B2 | 1/2019 | Victor et al. | |
| 10,222,787 B2 | 3/2019 | Romatier et al. | |
| 10,328,408 B2 | 6/2019 | Victor et al. | |
| 2002/0123864 A1 | 9/2002 | Eryurek et al. | 702/188 |
| 2002/0179495 A1 | 12/2002 | Heyse et al. | 208/137 |
| 2003/0036052 A1 | 2/2003 | Delwiche et al. | 435/4 |
| 2003/0105775 A1 | 6/2003 | Shimada | |
| 2003/0147351 A1 | 8/2003 | Greenlee | 370/232 |
| 2003/0223918 A1 | 12/2003 | Cammy | 422/144 |
| 2004/0079392 A1 | 4/2004 | Kuechler | 134/22.19 |
| 2004/0099572 A1 | 5/2004 | Evans | 208/113 |
| 2004/0109788 A1 | 6/2004 | Li et al. | 422/3 |
| 2004/0122273 A1 | 6/2004 | Kabin | 585/639 |
| 2004/0122936 A1 | 6/2004 | Mizelle et al. | |
| 2004/0147036 A1 | 7/2004 | Krenn et al. | 436/119 |
| 2004/0148144 A1 | 7/2004 | Martin | |
| 2004/0204775 A1 | 10/2004 | Keyes | 705/30 |
| 2004/0204913 A1 | 10/2004 | Mueller et al. | |
| 2004/0220689 A1 | 11/2004 | Mathur et al. | 700/97 |
| 2004/0220778 A1 | 11/2004 | Imai et al. | 702/188 |
| 2005/0027721 A1 | 2/2005 | Saenz | 707/100 |
| 2005/0029163 A1 | 2/2005 | Letzsch | 208/113 |
| 2005/0098033 A1 | 5/2005 | Mallavarapu et al. | 95/96 |
| 2005/0133211 A1 | 6/2005 | Osborn et al. | |
| 2005/0216209 A1 | 9/2005 | Evans | 702/45 |
| 2006/0020423 A1 | 1/2006 | Sharpe | 702/183 |
| 2006/0133412 A1 | 6/2006 | Callaghan | 370/465 |
| 2006/0252642 A1 | 11/2006 | Kanazirev | |
| 2006/0259163 A1 | 11/2006 | Hsiung et al. | 700/30 |
| 2007/0020154 A1 | 1/2007 | Evans | 422/139 |
| 2007/0059159 A1 | 3/2007 | Hjerpe | 415/117 |
| 2007/0059838 A1 | 3/2007 | Morrison et al. | 436/55 |
| 2007/0091824 A1 | 4/2007 | Budampati et al. | 370/255 |
| 2007/0091825 A1 | 4/2007 | Budampati et al. | 370/255 |
| 2007/0185664 A1 | 8/2007 | Tanaka | 702/56 |
| 2007/0192078 A1 | 8/2007 | Nasle et al. | 703/14 |
| 2007/0212790 A1 | 9/2007 | Welch et al. | 436/139 |
| 2007/0250292 A1 | 10/2007 | Alagappan et al. | 702/184 |
| 2007/0260656 A1 | 11/2007 | Wiig | |
| 2007/0271452 A1 | 11/2007 | Foo Kune et al. | 713/150 |
| 2008/0086322 A1 | 4/2008 | Wallace | 705/1 |
| 2008/0130902 A1 | 6/2008 | Foo Kune et al. | 380/286 |
| 2008/0154434 A1 | 6/2008 | Galloway et al. | |
| 2008/0217005 A1 | 9/2008 | Stluka et al. | 166/250.01 |
| 2008/0282606 A1 | 11/2008 | Plaza et al. | |
| 2009/0059786 A1 | 3/2009 | Budampati et al. | 370/230 |
| 2009/0060192 A1 | 3/2009 | Budampati et al. | 380/270 |
| 2009/0064295 A1 | 3/2009 | Budampati et al. | 726/6 |
| 2009/0201899 A1 | 8/2009 | Liu et al. | 370/338 |
| 2009/0204245 A1 | 8/2009 | Sustaeta | 700/99 |
| 2009/0245286 A1 | 10/2009 | Kore et al. | 370/475 |
| 2009/0268674 A1 | 10/2009 | Liu et al. | 370/329 |
| 2009/0281677 A1 | 11/2009 | Botich | 700/295 |
| 2010/0014599 A1 | 1/2010 | Holm et al. | 375/260 |
| 2010/0108567 A1 | 5/2010 | Medoff | 208/49 |
| 2010/0125347 A1 | 5/2010 | Martin et al. | 700/31 |
| 2010/0152900 A1 | 6/2010 | Gurciullo et al. | |
| 2010/0158764 A1 | 6/2010 | Hedrick | 422/134 |
| 2010/0230324 A1 | 9/2010 | Al-Alloush et al. | 208/82 |
| 2010/0262900 A1 | 10/2010 | Romatier et al. | 715/219 |
| 2011/0112659 A1 | 5/2011 | Pachner et al. | 700/29 |
| 2011/0152590 A1 | 6/2011 | Sadler et al. | 585/313 |
| 2011/0152591 A1 | 6/2011 | Sadler et al. | 585/313 |
| 2011/0311014 A1 | 12/2011 | Hottovy et al. | 376/283 |
| 2012/0029966 A1 | 2/2012 | Cheewakriengkrai et al. | 705/7.25 |

(56) References Cited

U.S. PATENT DOCUMENTS

| | | | |
|---|---|---|---|
| 2012/0083933 A1 | 4/2012 | Subbu et al. | 700/291 |
| 2012/0095808 A1 | 4/2012 | Kattapuram et al. | 705/7.37 |
| 2012/0104295 A1 | 5/2012 | Do et al. | 251/129.01 |
| 2012/0121376 A1 | 5/2012 | Huis in Het Veld | 415/1 |
| 2012/0123583 A1 | 5/2012 | Hazen et al. | |
| 2012/0197616 A1 | 8/2012 | Trnka | 703/6 |
| 2012/0259583 A1 | 10/2012 | Noboa et al. | |
| 2013/0029587 A1 | 1/2013 | Gandhi et al. | 455/7 |
| 2013/0031960 A1 | 2/2013 | Delrahim | 73/40.5 R |
| 2013/0079899 A1 | 3/2013 | Baramov | 700/32 |
| 2013/0090088 A1 | 4/2013 | Chevsky et al. | 455/411 |
| 2013/0094422 A1 | 4/2013 | Thanikachalam | 370/312 |
| 2013/0172643 A1 | 7/2013 | Pradeep | 585/310 |
| 2013/0253898 A1 | 9/2013 | Meagher et al. | 703/18 |
| 2013/0270157 A1 | 10/2013 | Ferrara | 208/48 AA |
| 2013/0311437 A1 | 11/2013 | Stluka et al. | 707/706 |
| 2013/0327052 A1 | 12/2013 | O'Neill | 60/772 |
| 2014/0008035 A1 | 1/2014 | Patankar et al. | |
| 2014/0026598 A1 | 1/2014 | Trawicki | 62/56 |
| 2014/0074273 A1 | 3/2014 | Mohideen et al. | 700/98 |
| 2014/0114039 A1 | 4/2014 | Benham et al. | 526/348.5 |
| 2014/0131027 A1 | 5/2014 | Chir | 165/300 |
| 2014/0163275 A1 | 6/2014 | Yanagawa et al. | 585/319 |
| 2014/0179968 A1 | 6/2014 | Yanagawa et al. | 585/476 |
| 2014/0212978 A1 | 7/2014 | Sharpe, Jr. et al. | 436/6 |
| 2014/0294683 A1 | 10/2014 | Siedler | 422/129 |
| 2014/0294684 A1 | 10/2014 | Siedler | 422/129 |
| 2014/0296058 A1 | 10/2014 | Sechrist et al. | 502/53 |
| 2014/0309756 A1 | 10/2014 | Trygstad | 700/31 |
| 2014/0337256 A1 | 11/2014 | Varadi et al. | 706/12 |
| 2014/0337277 A1 | 11/2014 | Asenjo et al. | |
| 2015/0059714 A1 | 3/2015 | Bernards | 123/568.11 |
| 2015/0060331 A1 | 3/2015 | Sechrist et al. | |
| 2015/0077263 A1 | 3/2015 | Ali et al. | 340/679 |
| 2015/0078970 A1 | 3/2015 | Iddir et al. | 422/218 |
| 2015/0098862 A1 | 4/2015 | Lok et al. | 422/49 |
| 2015/0158789 A1 | 6/2015 | Keusenkothen | 60/780 |
| 2015/0185716 A1 | 7/2015 | Wichmann et al. | 700/287 |
| 2015/0276208 A1 | 10/2015 | Maturana et al. | 700/274 |
| 2015/0284641 A1 | 10/2015 | Shi | 208/113 |
| 2015/0330571 A1 | 11/2015 | Beuneken | 141/4 |
| 2016/0033941 A1 | 2/2016 | T et al. | 700/81 |
| 2016/0048119 A1 | 2/2016 | Wojsznis | 700/11 |
| 2016/0098037 A1 | 4/2016 | Zornio et al. | 700/20 |
| 2016/0098234 A1 | 4/2016 | Weaver | 358/1.15 |
| 2016/0122663 A1 | 5/2016 | Pintar et al. | |
| 2016/0147204 A1 | 5/2016 | Wichmann et al. | 700/287 |
| 2016/0237910 A1 | 8/2016 | Saito | |
| 2016/0260041 A1 | 9/2016 | Horn et al. | |
| 2016/0291584 A1 | 10/2016 | Horn et al. | |
| 2016/0292188 A1 | 10/2016 | Horn et al. | |
| 2016/0292325 A1 | 10/2016 | Horn et al. | |
| 2016/0313653 A1 | 10/2016 | Mink | |
| 2016/0363315 A1 | 12/2016 | Colannino et al. | |
| 2017/0009932 A1 | 1/2017 | Oh | |
| 2017/0058213 A1 | 3/2017 | Oprins | 585/303 |
| 2017/0082320 A1 | 3/2017 | Wang | |
| 2017/0107188 A1 | 4/2017 | Kawaguchi | |
| 2017/0284410 A1 | 10/2017 | Sharpe, Jr. | |
| 2017/0315543 A1 | 11/2017 | Horn et al. | |
| 2017/0323038 A1 | 11/2017 | Horn et al. | |
| 2017/0352899 A1 | 12/2017 | Asai | |
| 2018/0046155 A1 | 2/2018 | Horn et al. | |
| 2018/0081344 A1 | 3/2018 | Romatier et al. | |
| 2018/0082569 A1 | 3/2018 | Horn et al. | |
| 2018/0121581 A1 | 5/2018 | Horn et al. | |
| 2018/0122021 A1 | 5/2018 | Horn et al. | |
| 2018/0155638 A1 | 6/2018 | Al-Ghamdi | 208/79 |
| 2018/0155642 A1 | 6/2018 | Al-Ghamdi et al. | |
| 2018/0197350 A1 | 7/2018 | Kim | |
| 2018/0275690 A1 | 9/2018 | Lattanzio et al. | |
| 2018/0275691 A1 | 9/2018 | Lattanzio et al. | |
| 2018/0275692 A1 | 9/2018 | Lattanzio et al. | |
| 2018/0280914 A1 | 10/2018 | Victor et al. | |
| 2018/0280917 A1 | 10/2018 | Victor et al. | |
| 2018/0282633 A1 | 10/2018 | Van de Cotte et al. | |
| 2018/0282634 A1 | 10/2018 | Van de Cotte et al. | |
| 2018/0282635 A1 | 10/2018 | Van de Cotte et al. | |
| 2018/0283368 A1 | 10/2018 | Van de Cotte et al. | |
| 2018/0283392 A1 | 10/2018 | Van de Cotte et al. | |
| 2018/0283404 A1 | 10/2018 | Van de Cotte et al. | |
| 2018/0283811 A1 | 10/2018 | Victor et al. | |
| 2018/0283812 A1 | 10/2018 | Victor et al. | |
| 2018/0283813 A1 | 10/2018 | Victor et al. | |
| 2018/0283815 A1 | 10/2018 | Victor et al. | |
| 2018/0283816 A1 | 10/2018 | Victor et al. | |
| 2018/0283818 A1 | 10/2018 | Victor et al. | |
| 2018/0284705 A1 | 10/2018 | Van de Cotte et al. | |
| 2018/0286141 A1 | 10/2018 | Van de Cotte et al. | |
| 2018/0311609 A1 | 11/2018 | McCool et al. | |
| 2018/0362862 A1 | 12/2018 | Gellaboina et al. | |
| 2018/0363914 A1 | 12/2018 | Faiella et al. | |
| 2018/0364747 A1 | 12/2018 | Charr et al. | |
| 2019/0002318 A1 | 1/2019 | Thakkar et al. | |
| 2019/0003978 A1 | 1/2019 | Shi et al. | |
| 2019/0015806 A1 | 1/2019 | Gellaboina et al. | |
| 2019/0041813 A1 | 2/2019 | Horn et al. | |
| 2019/0083920 A1 | 3/2019 | Bjorklund et al. | |
| 2019/0101336 A1 | 4/2019 | Victor et al. | |
| 2019/0101342 A1 | 4/2019 | Victor et al. | |
| 2019/0101907 A1 | 4/2019 | Charr et al. | |
| 2019/0102966 A1 | 4/2019 | Lorenz | |
| 2019/0108454 A1 | 4/2019 | Banerjee et al. | |
| 2019/0120810 A1 | 4/2019 | Kumar KN et al. | |
| 2019/0151814 A1 | 5/2019 | Victor et al. | |
| 2019/0155259 A1 | 5/2019 | Romatier et al. | |

FOREIGN PATENT DOCUMENTS

| | | | | |
|---|---|---|---|---|
| EP | | 2801937 A1 | 11/2014 | G06Q 10/06 |
| GB | | 1134439 A | 11/1968 | G01N 31/22 |
| WO | WO 1990/010083 A1 | | 9/1990 | C12Q 1/04 |
| WO | WO 2001/060951 A1 | | 8/2001 | C10G 51/04 |
| WO | WO 2006/044408 A1 | | 4/2006 | F23D 14/72 |
| WO | WO 2007/095585 A2 | | 8/2007 | A61K 31/721 |
| WO | WO 2009/046095 A1 | | 4/2009 | G06F 11/00 |
| WO | WO 2014/042508 A1 | | 3/2014 | G06Q 50/04 |
| WO | WO 2014/123993 A1 | | 8/2014 | G06F 17/00 |
| WO | WO 2016/141128 A1 | | 9/2016 | G06Q 10/06 |
| WO | WO 2017/079058 A1 | | 5/2017 | B01D 1/14 |

OTHER PUBLICATIONS

Google Search Results, Jun. 1, 2021, 1 pp. (Year: 2021).*
Bespalov A. V. et al., Control systems of chemical and technological processes, pp. 508-509 (2001) (Russian).
Daniel Goebel, Dry Gas Seal Contamination During Operation and Pressurization Hold, [online], Feb. 2016, [retrieved on Jun. 19, 2019]. Retrieved from <https://core.ac.uk/download/pdf/84815277.pdf> (Year: 2016).
EnergyMedor®, Product brochure (Nov. 2014).
Chistof Huber, Density and Concentration Measurement Application for Novel MEMS-based Micro Densitometer for Gas, [online], 2016, [retrieved on Jun. 19, 2019]. Retrieved from <https://www.ama-science.org/proceedings/getFile/ZwZ1 BD==> (Year: 2016).
Lotters, Real-time Composition Determination of Gas Mixtures, [online], 2015, [retrieved on Jun. 19, 2019]. Retrieved from <https://www.ama-science.org/proceedings/getFile/ZwNOZj==>(Year: 2015).
Maybeck, Peter S., "Stochastic models, estimation, and control," vol. 1, Academic Press (1979), 19 pages.
Stanhope-Seta, "Seta Existent Gum Solid Bath," Technical Information, 12200-3, Particulates, Residues & Composition, Jun. 2010, 1 page.
Fess, "Recent Developments in Sulfur Analysis," Article Notes, American Laboratory, Jan. 2013, 5 pages.
Tanaka Scientific Limited, "Automatic Conradson Carbon Residue Tester ACR-6," Specification, Automatic Petroleum Tester, Jun. 2014, 2 pages.
Tanaka Scientific Limited, "Micro Carbon Residue Tester ACR-M3," Specification, Automatic Petroleum Tester, Jun. 2014, 2 pages.
Stanhope-Seta, "Micro Carbon Residue Tester, Micro Carbon Resi-

(56) References Cited

OTHER PUBLICATIONS due of Petroleum Products, ASTM D4530-IP398; ISO 10370," Brochure, Micro Carbon Residue, Dec. 2015, 2 pages.

Applied Rigaku Technologies, "Elemental analysis by X-ray fluorescence," Brochure, NEX CG Petroleum, Nov. 2014, 8 pages.

Digitalrefining.com, "Ilsky refinery optimizes crude distillation unit processing with Experion® HS system," Article, Nov. 2016, 3 pages.

Labequip, "K27100 Ramsbottom Carbon Residue Apparatus & Data Acquisition Software," Koehler product information, May 2017, 3 pages.

Labequip, "Determination of Carbon Residue (Micro Conradson Method)," Koehler product information, May 2017, 2 pages.

Emerson Process Management, "Micro Motion Fort Viscosity Meter," Brochure, MC-001864 Rev A, Jan. 2014, 6 pages.

Emerson Process Management, "Micro Motion Ford Density Meter," Brochure, MC-001865 Rev E, Jul. 2017, 6 pages.

\* cited by examiner
† cited by third party

US 11,105,787 B2

SYSTEM AND METHOD TO OPTIMIZE CRUDE OIL DISTILLATION OR OTHER PROCESSING BY INLINE ANALYSIS OF CRUDE OIL PROPERTIES

CROSS-REFERENCE TO RELATED APPLICATION AND PRIORITY CLAIM

This application claims priority under 35 U.S.C. § 119(e) to U.S. Provisional Patent Application No. 62/575,171 filed on Oct. 20, 2017. This provisional application is hereby incorporated by reference in its entirety.

TECHNICAL FIELD

This disclosure relates generally to industrial process control and automation systems. More specifically, this disclosure relates to a system and method to optimize crude oil distillation or other processing by inline analysis of crude oil properties.

BACKGROUND

There are various types or qualities of crude oil that can be processed by oil and gas refineries. "Sweet" crude oil can be defined as petroleum having a sulfur content less than 0.50% by weight, while "sour" crude oil can be defined as petroleum having a sulfur content at or above 0.50% by weight. Other thresholds for the sulfur content can also be used, such as 0.42% by weight. Light sweet crude oil is typically the most sought-after version of crude oil since it can be directly refined into gasoline, kerosene, and high-quality diesel fuel. Sour crude oil typically needs to be processed to remove the impurities before being refined into finished products.

SUMMARY

This disclosure provides a system and method to optimize crude oil distillation or other processing by inline analysis of crude oil properties.

In a first embodiment, a method includes obtaining inline measurements of one or more properties of crude oil. The method also includes translating the measurements into a set of process and control parameters. The method further includes applying the process and control parameters to process equipment. The process and control parameters configure the process equipment to process the crude oil having the one or more properties.

In a second embodiment, an apparatus includes at least one processor configured to obtain inline measurements of one or more properties of crude oil, translate the measurements into a set of process and control parameters, and apply the process and control parameters to process equipment. The process and control parameters configure the process equipment to process the crude oil having the one or more properties.

In a third embodiment, a non-transitory computer readable medium contains instructions that, when executed, cause at least one processing device to obtain inline measurements of one or more properties of crude oil, translate the measurements into a set of process and control parameters, and apply the process and control parameters to process equipment. The process and control parameters configure the process equipment to process the crude oil having the one or more properties.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
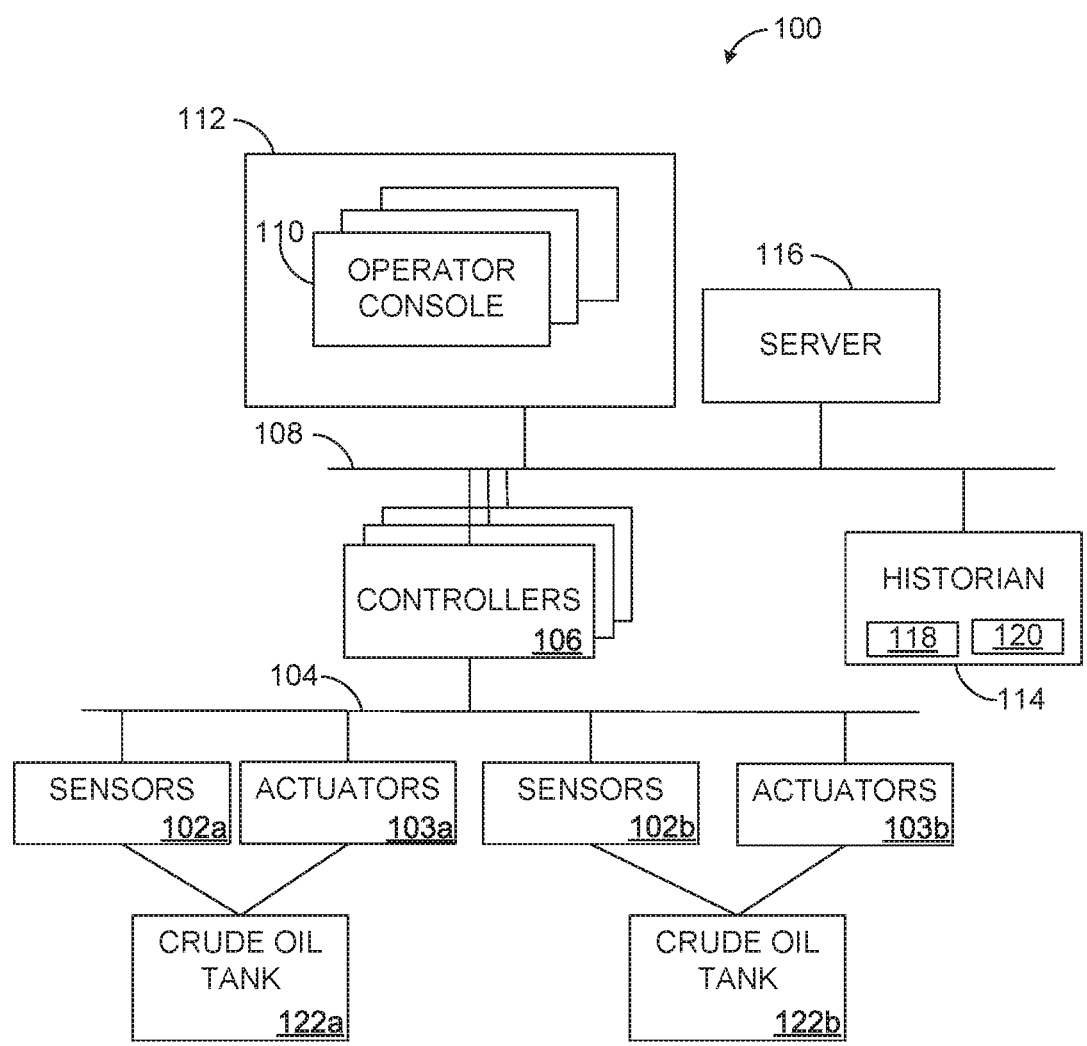
FIG. 1 illustrates an example industrial process control and automation system supporting inline analysis of crude oil properties according to this disclosure.

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

As noted above, there are various types or qualities of crude oil that can be processed by oil and gas refineries, such as sweet crude oil, sour crude oil, and mixtures thereof. Sour crude oil and mixtures that contain sour crude oil typically require more processing, often in the form of hydro-treating operations performed on the crude oil, to be refined compared to sweet crude oil. One important factor in determining the profitability of an oil and gas refinery is the ability of the refinery to process different types or qualities of crude oil. A refinery can typically earn larger profits when processing lower-cost sour crude oil (or mixtures that contain sour crude oil) compared to processing higher-cost sweet crude oil. The ability to process sour crude oil is also becoming more important as the quality of sweet crude oil reserves continues to drop over time, pushing the price of sweet crude oil upwards. Moreover, refineries often receive and store (and sometimes blend) crude oil of varying types or qualities as the crude oil is purchased on the spot market. In many cases, refineries often end up processing multiple types or qualities of crude oil in a given time period (such as a day, week, or month).

In order to remain competitive and achieve improved profit levels, many oil and gas refineries need to have both (i) the ability to process sour crude oil or blends that contain sour crude oil and (ii) the ability to seamlessly switch between processing different types or qualities of crude oil. Unfortunately, there is a clear gap in existing refinery automation solutions when it comes to supporting seamless switches in processing crude oil types or qualities. Namely, crude oil composition and crude oil consistency are analyzed offline, and the results are then provided to a process control and automation system for use. Crude oil in its natural and unrefined state exhibits significant variations in physical and chemical properties, and crude oil can be treated differently using different refining processes depending on its physical and chemical properties. In many instances, refineries can process different types of crude oil over time by tuning the refining lines in the refineries based on the offline characterizations of the crude oil. However, there can be significant time delays between the receipt of crude oil and the offline characterizations of the crude oil, so the tuning of the refining lines can also be delayed. Also, refineries today typically follow well-established manual or semi-automated process steps to ensure a smooth switchover of crude oil feeds, but this takes a good amount of time and effort and can invite errors due to a lack of automation.

This disclosure provides various techniques supporting in-line sensing and translation of crude oil properties, such as crude oil being processed in a refinery. The in-line sensing can detect various properties of the crude oil, such as the crude oil's physical and chemical properties. Example properties of crude oil that can be detected include the crude oil's density or specific gravity, viscosity, carbon residue, and sulfur content. The translation allows the crude oil's properties to be used to identify a set of process and control parameters of equipment, such as a crude oil distillation column or other equipment in a refining line of the refinery. Thus, the translation can be performed to tune (and likely repeatedly re-tune) the process equipment to suit the crude oil being received by the equipment. As a result, process corrections can be automatically applied to a refinery process or other process to compensate for the varying properties of the crude oil.

The ability to sense the properties of crude oil, translate the crude oil's properties into process and control parameters, and automatically adjust equipment using the parameters can greatly simplify feed switchovers or other operations in refineries or other facilities. Also, the ability to automatically apply process corrections can result in substantial time and cost savings for equipment owners or operators as well as their customers. In addition, the ability to quickly and easily perform feed switchovers can help refineries or other facilities deal with crude oil having constantly-changing properties, which may be common when different types or qualities of crude oil are purchased on the spot market, stored, and possibly blended.

In this document, a "process parameter" generally refers to a parameter describing an industrial process (such as a refining process) to be controlled, where that parameter can be considered during control operations. Example types of process parameters include process delay times, process dead times, process time constants, and process gains. A "control parameter" generally refers to a parameter describing or affecting control of equipment (such as a distillation column or blending unit in a refinery), where that parameter can affect how control operations are performed. Example types of control parameters include times for reaching desired setpoints, settling times for process variables, control horizons, and allowable limits on changes to an industrial process.

FIG. 1 illustrates an example industrial process control and automation system 100 supporting inline analysis of crude oil properties according to this disclosure. As shown in FIG. 1, the system 100 includes various components that facilitate production or processing of at least one product or other material, such as crude oil. For instance, the system 100 can be used to facilitate control over components in one or multiple oil and gas refineries or other industrial plants. Each plant represents one or more processing facilities (or one or more portions thereof). In general, each plant may implement one or more industrial processes and can individually or collectively be referred to as a process system. A process system generally represents any system or portion thereof configured to process one or more products or other materials in some manner. As a particular example, a process system could include one or more oil and gas refineries, where each refinery has one or more refining lines for processing crude oil.

In the example shown in FIG. 1, the system 100 includes one or more sensors 102a-102b and one or more actuators 103a-103b. The sensors 102a-102b and actuators 103a-103b represent components in a process system that may perform any of a wide variety of functions. For example, the sensors 102a-102b could measure a wide variety of characteristics in the process system, such as pressure, temperature, or flow rate. Also, the actuators 103a-103b could alter a wide variety of characteristics in the process system. Each of the sensors 102a-102b includes any suitable structure for measuring one or more characteristics in a process system. Each of the actuators 103a-103b includes any suitable structure for operating on or affecting one or more conditions in a process system.

As described in more detail below, the sensors 102a-102b include one or more inline sensors configured to measure one or more properties of crude oil, such as one or more physical or chemical properties of the crude oil. For example, the sensors 102a-102b could include a density or specific gravity meter, a viscosity meter, a sulfur content measurement device, or a carbon residue measurement device for measuring one or more properties of crude oil. Depending on the implementation, any one of these types of sensors or any combination of these types of sensors (including all of these types of sensors) could be used. In particular embodiments, the sensors 102a-102b can measure density or specific gravity at standard operating conditions (such as at a specific temperature like about 59° F. or 15° C.), viscosity, sulfur content, and carbon residue of crude oil. When a carbon residue measurement device is used, the carbon residue measurements can represent Ramsbottom carbon residue (RCR), Conradson carbon residue (CCR), micro carbon residue (MCR), or other suitable measurements.

The actuators 103a-103b can also include one or more devices configured to operate on or process crude oil. For example, an actuator 103a-103b could be used to pump crude oil into, out of, or through a structure. An actuator 103a-103b could also be used to stir or blend crude oil in a structure. Further, an actuator 103a-103b could be used to heat crude oil in a structure. In addition, a collection of actuators 103a-103b could be used to refine crude oil, such as in a crude oil distillation column.

In some embodiments, different sensors and actuators can be associated with different storage tanks 122a-122b or other structures in which crude oil is stored, transported, or processed. In this example, the sensor 102a and the actuator 103a are associated with the storage tank 122a, and the sensor 102b and the actuator 103b are associated with the storage tank 122b. Here, the sensor 102a can take inline measurements of the crude oil in the storage tank 122a, such as by capturing real-time (non-laboratory) measurements of the crude oil in the storage tank 122a. Similarly, the sensor 102b can take inline measurements of the crude oil in the storage tank 122b, such as by capturing real-time (non-laboratory) measurements of the crude oil in the storage tank 122b. Note, however, that the use of the sensors 102a-102b in the tanks 122a-122b is not required. In other embodiments, for example, the sensors 102a-102b could be used to capture measurements of crude oil passing through pipes or other structures or into or out of one or more tanks 122a-122b or other equipment. As particular examples, the crude oil from one or more of the tanks 122a-122b could be provided to a crude oil distillation column, and one or more sensors 102a-102b could take measurements associated with crude oil flowing through pipes leading to the distillation column or crude oil flowing into or within the distillation column.

At least one network 104 is coupled to the sensors 102a-102b and actuators 103a-103b. The network 104 facilitates interaction with the sensors 102a-102b and actuators 103a-103b. For example, the network 104 could transport measurement data from the sensors 102a-102b and provide control signals to the actuators 103a-103b. The network 104 could represent any suitable network or combination of networks. As particular examples, the network 104 could represent at least one Ethernet network, electrical signal network (such as a HART network), pneumatic control signal network, or any other or additional type(s) of network(s).

The system 100 also includes one or more controllers 106. The controllers 106 can be used in the system 100 to perform various functions in order to control one or more industrial processes. For example, a first set of controllers 106 may use measurements from one or more sensors 102a-102b to control the operation of one or more actuators 103a-103b. A second set of controllers 106 could be used to optimize the control logic or other operations performed by the first set of controllers. A third set of controllers 106 could be used to perform additional functions. As a particular example, one or more of the controllers 106 could obtain measurements of crude oil properties, translate the crude oil properties, and tune process and control parameters. One or more other controllers 106 or other equipment could then receive the tuned process and control parameters and use the parameters. The controllers 106 can communicate via one or more networks 108 and associated switches, firewalls, and other components.

Each controller 106 includes any suitable structure for controlling one or more aspects of an industrial process. At least some of the controllers 106 could, for example, represent proportional-integral-derivative (PID) controllers or multivariable controllers, such as controllers implementing model predictive control or other advanced predictive control. As a particular example, each controller 106 could represent a computing device running a real-time operating system, a WINDOWS operating system, or other operating system.

Operator access to and interaction with the controllers 106 and other components of the system 100 can occur via various operator consoles 110. Each operator console 110 could be used to provide information to an operator and receive information from an operator. For example, each operator console 110 could provide information identifying a current state of an industrial process to the operator, such as values of various process variables and alarms associated with the industrial process. Each operator console 110 could also receive information affecting how the industrial process is controlled, such as by receiving setpoints or control modes for process variables controlled by the controllers 106 or other information that alters or affects how the controllers 106 control the industrial process. Each operator console 110 includes any suitable structure for displaying information to and interacting with an operator. For example, each operator console 110 could represent a computing device running a WINDOWS operating system or other operating system.

Multiple operator consoles 110 can be grouped together and used in one or more control rooms 112. Each control room 112 could include any number of operator consoles 110 in any suitable arrangement. In some embodiments, multiple control rooms 112 can be used to control an industrial plant, such as when each control room 112 contains operator consoles 110 used to manage a discrete part of a refinery or other industrial plant.

The control and automation system 100 here also includes at least one historian 114 and one or more servers 116. The historian 114 represents a component that stores various information about the system 100. The historian 114 could, for instance, store information that is generated by the various controllers 106 during the control of one or more industrial processes. The historian 114 could also store information generated by the sensors 102a-102b, such as measurements of incoming crude oil over time. The historian 114 includes any suitable structure for storing and facilitating retrieval of information. Although shown as a single component here, the historian 114 could be located elsewhere in the system 100, or multiple historians could be distributed in different locations in the system 100.

Each server 116 denotes a computing device that executes applications for users of the operator consoles 110 or other applications. The applications could be used to support various functions for the operator consoles 110, the controllers 106, or other components of the system 100. As a particular example, one or more of the servers 116 could obtain measurements of crude oil properties, translate the crude oil properties, and tune process and control parameters. One or more controllers 106 or other equipment could then receive the tuned process and control parameters and use the parameters. Each server 116 could represent a computing device running a WINDOWS operating system or other operating system.

Various events that occur in an industrial process control and automation system (such as the system 100) are logged into one or more alarm and event logs 118, which can be stored in the historian 114. The values of process variables over time can also be recorded and stored in one or more process variable history logs 120, which can be stored in the historian 114. For example, one or more process variable history logs 120 could store density or specific gravity, viscosity, carbon residue, sulfur content, or other measurements captured by the sensors 102a-102b over time.

The overall viability or economics of an oil and gas refinery may often depend on the interaction of three elements: the choice of the crude oil received and processed (referred to as "crude slates"), the complexity of the refining equipment (referred to as "refinery configuration"), and the desired type and quality of end product(s) produced (referred to as "product slate"). Lighter crude oil is expensive but requires less refinery investments, while heavier crude oil is cheaper but requires a more expensive refining process. Many refineries are built in such a way that they can process a wide range of crude oil types or qualities, such as sweet crude oil, sour crude oil, and mixtures thereof. This can be important or essential for making profitable business decisions in a varying crude oil market. In such a refinery, the switching of a crude oil feed is performed quite often, and this operation typically requires re-tuning of process and control parameters for refining equipment to suit the respective crude oil being received and refined.

Currently, a crude oil composition analysis, consistency analysis, or other analysis is done completely offline in a laboratory environment, and the results are fed into a control system in the form of a stored database. As noted above, refineries can follow well-established manual or semi-automated process steps to help ensure a smooth switchover of crude oil feeds, but this takes effort and time and can introduce errors. As a result, there exists an opportunity to automate the inline characterization of both physical and chemical properties of incoming crude oil to seamlessly reconfigure a refinery process or other process and the controls for that process. Such an automated system could function as a batch process overlay on a continuous process refining line, where recipes are decided based on the incoming crude oil. In reality, wide ranges of crude oil (with varying densities and compositions) are traded in global markets, and refineries often conduct spot buys to purchase and store crude oil based on cost and availability. Such dynamics in buying crude oil can make the refining process complex, possibly including several switchovers of crude oil feeds in a short time period.

As described in more detail below, embodiments of this disclosure provide inline analysis of crude oil properties, where the properties of crude oil can be measured in-line and then translated into a set of appropriate process and control parameters. The actual process and control parameters of equipment, such as a crude oil distillation column or other equipment in a refining line of a refinery or other facility, can then be tuned to account for the current crude oil properties. Thus, embodiments of this disclosure provide automation to refining or other processes by employing in-line sensing to and translation of crude oil properties and applying necessary or desired process corrections to the process. Additional details regarding these techniques are provided below.

Although FIG. 1 illustrates one example of an industrial process control and automation system 100, various changes may be made to FIG. 1. For example, the system 100 could include any number of sensors, actuators, controllers, networks, operator stations, control rooms, historians, servers, storage tanks, and other components. Also, the makeup and arrangement of the system 100 in FIG. 1 is for illustration only. Components could be added, omitted, combined, further subdivided, or placed in any other suitable configuration according to particular needs. Further, particular functions have been described as being performed by particular components of the system 100. This is for illustration only. In general, control and automation systems are highly configurable and can be configured in any suitable manner according to particular needs. In addition, FIG. 1 illustrates one example operational environment where inline analysis of crude oil properties can be used in an industrial process and control and automation system. This functionality can be used in any other suitable system.

Figure 2:
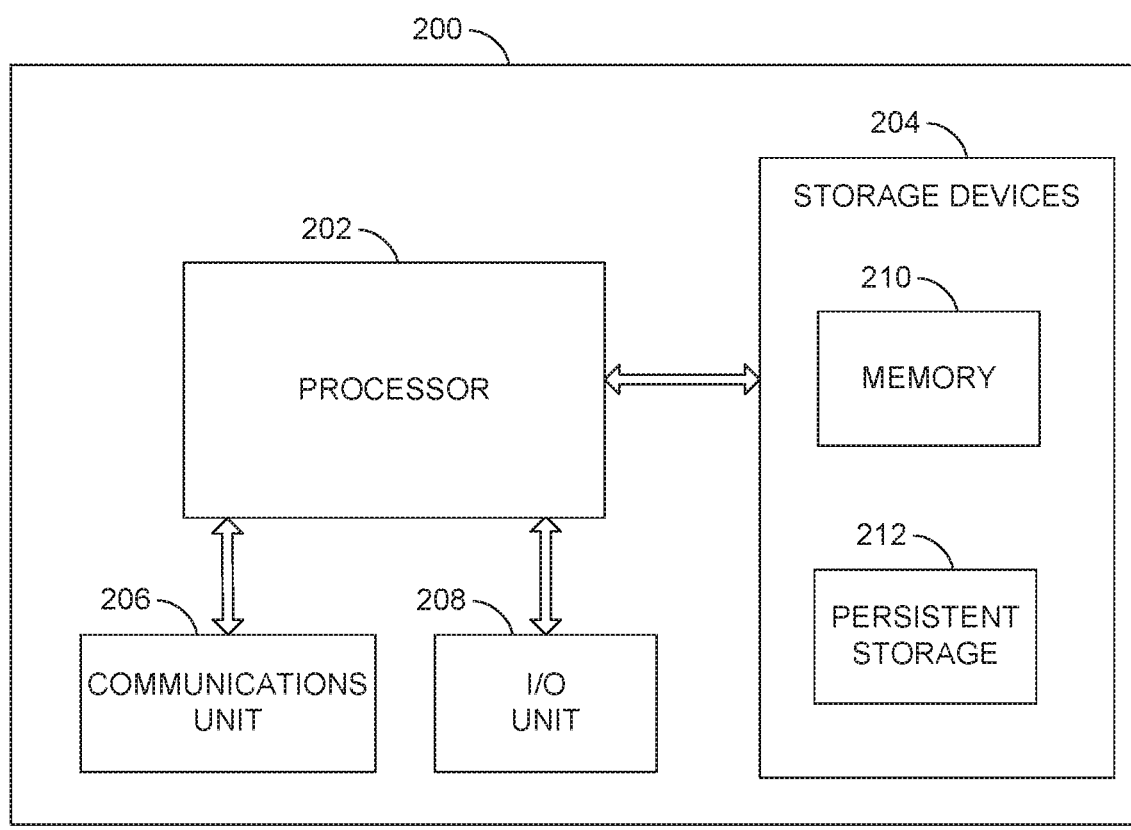
FIG. 2 illustrates an example computing device supporting inline analysis of crude oil properties according to this disclosure.

FIG. 2 illustrates an example computing device 200 supporting inline analysis of crude oil properties according to this disclosure. The device 200 could, for example, represent any of the computing devices shown in FIG. 1 and described above, such as a controller 106, operator console 110, or server 116. However, the device 200 could represent any other suitable computing system supporting inline analysis of crude oil properties.

As shown in FIG. 2, the device 200 includes at least one processor 202, at least one storage device 204, at least one communications unit 206, and at least one input/output (I/O) unit 208. Each processor 202 can execute instructions, such as those that may be loaded into a memory 210. Each processor 202 denotes any suitable processing device, such as one or more microprocessors, microcontrollers, digital signal processors, application specific integrated circuits (ASICs), field programmable gate arrays (FPGAs), or discrete circuitry.

The memory 210 and a persistent storage 212 are examples of storage devices 204, which represent any structure(s) capable of storing and facilitating retrieval of information (such as data, program code, and/or other suitable information on a temporary or permanent basis). The memory 210 may represent a random access memory or any other suitable volatile or non-volatile storage device(s). The persistent storage 212 may contain one or more components or devices supporting longer-term storage of data, such as a read only memory, hard drive, Flash memory, or optical disc.

The communications unit 206 supports communications with other systems or devices. For example, the communications unit 206 could include at least one network interface card or wireless transceiver facilitating communications over at least one wired or wireless network. As a particular example, the communications unit 206 could support communications with one or more sensors 102a-102b or one or more actuators 103a-103b over the network 104. As another particular example, the communications unit 206 could support communications with a controller 106, operator console 110, historian 114, or server 116 over the network 108. The communications unit 206 may support communications through any suitable physical or wireless communication link(s).

The I/O unit 208 allows for input and output of data. For example, the I/O unit 208 may provide a connection for user input through a keyboard, mouse, keypad, touchscreen, or other suitable input device. The I/O unit 208 may also send output to a display, printer, or other suitable output device. Note, however, that the use of the I/O unit 208 for local I/O may not be needed, such as when the device 200 is accessible locally or remotely over a network connection.

As described in more detail below, the device 200 can be used to support the inline analysis of crude oil properties. For example, the storage device 204 could store, and the processor 202 could execute, instructions that receive sensor measurement data and translate that sensor measurement data into a suitable set of process and control parameters for equipment. In some embodiments, one or more models can be used to identify the process and control parameters. A model generally defines a mathematical relationship between at least two variables, such as one or more crude oil properties and one or more process and control parameters. A model that considers multiple inputs in order to generate one or more outputs is often referred to as a multivariable model. One or multiple models could be used here depending on the implementation, and each model may or may not be a multivariable model. Also, in some embodiments, the storage device 204 could store, and the processor 202 could execute, instructions that support data analytics and machine learning. The data analytics can be used to analyze the sensor measurements and to process the sensor measurements in desired ways. The machine learning can be used to translate the sensor measurements into the process and control parameters and to adjust the models, data analytics, or other logic used to identify the process and control parameters over time. Note, however, that these functions can be implemented in any other suitable manner.

Although FIG. 2 illustrates one example of a computing device 200 supporting inline analysis of crude oil properties, various changes may be made to FIG. 2. For example, various components in FIG. 2 could be combined, further subdivided, or omitted and additional components could be added according to particular needs. Also, computing devices can come in a wide variety of configurations, and FIG. 2 does not limit this disclosure to any particular configuration of computing device.

Figure 3:
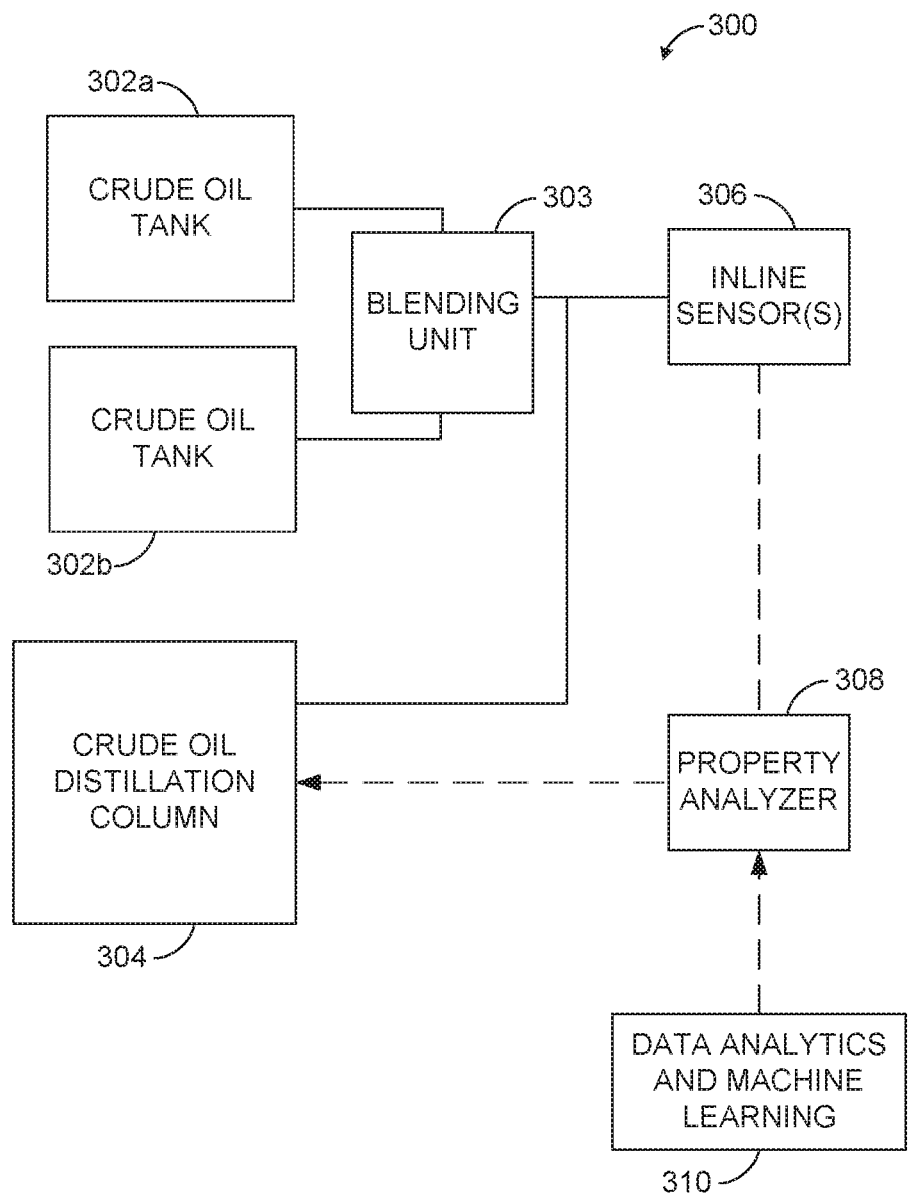
FIG. 3 illustrates an example system supporting inline analysis of crude oil properties in a process control and automation system according to this disclosure.

FIG. 3 illustrates an example system 300 supporting inline analysis of crude oil properties in a process control and automation system according to this disclosure. The system 300 could, for example, be used for analyzing crude oil in the industrial process control and automation system 100 of FIG. 1. However, the system 300 could be used with any other suitable industrial process control and automation system.

As shown in FIG. 3, the system 300 includes one or more crude oil storage tanks 302a-302b, which could represent the tanks 122a-122b in FIG. 1 described above. Each storage tank 302a-302b generally represents any suitable structure configured to receive and hold crude oil. Each of the storage tanks 302a-302b can be used to hold sweet crude oil, sour crude oil, or a blend or mixture containing different types or qualities of crude oil (often times including sour crude oil).

Optionally, crude oil from multiple tanks 302a-302b can be provided to at least one blending unit 303. The blending unit 303 generally operates to mix crude oil from multiple tanks 302a-302b before the crude oil is passed to other components for processing. In some embodiments, the blending unit 303 operates to mix crude oil streams from the tanks 302a-302b at a user-specified or other mixing ratio. As described below, the mixing ratio can be adjusted in order to provide desired functionality in the system 300. This may be useful, for example, when the crude oil in the multiple tanks 302a-302b has different physical or chemical properties, and blending the crude oil in the tanks 302a-302b at a certain ratio can help to achieve desired properties in the blend. The blending unit 303 includes any suitable structure configured to mix or blend crude oil.

Crude oil from one or more of the tanks 302a-302b or blending units 303 can be provided to equipment used to refine or otherwise process the crude oil. In this example, the crude oil is provided to a crude oil distillation column 304. Crude oil from a single tank 302a or 302b can be provided to the distillation column 304, or a blend of crude oil from multiple tanks 302a-302b can be provided to the distillation column 304. The distillation column 304 performs distillation operations on the crude oil to help refine the crude oil into one or more finished products, such as gasoline, kerosene, or diesel fuel. If needed, hydro-treating operations can be performed on the crude oil prior to or within the distillation column 304, such as to support the processing of sour crude oil or blends containing sour crude oil. Various types of crude oil distillation columns are known in the art. One or more of the controllers 106 in FIG. 1 (and often times a number of controllers 106) can be used to control and vary the operation of the distillation column 304.

One or more inline sensors 306 are configured to capture measurements of one or more properties of crude oil in the system 300. The inline sensors 306 could represent the sensors 102a-102b in FIG. 1 described above. The inline sensors 306 are used here to capture measurements of crude oil properties for crude oil that is stored in the tank(s) 302a-302b or being sent from the tank(s) 302a-302b or blending unit 303 to the distillation column 304. For example, the inline sensors 306 can be used to sense one or more properties of crude oil within one or more structures in which the crude oil is stored, transported, or processed. Each inline sensor 306 could be positioned within a tank 302a-302b, pipe, or other structure, or each inline sensor 306 could be attached to (but positioned outside of) a tank 302a-302b, pipe, or other structure. Each inline sensor 306 can generally be positioned in any suitable location where the inline sensor 306 can obtain a sample of crude oil.

The inline sensors 306 could capture any suitable measurements of crude oil properties, such as crude oil's density or specific gravity, viscosity, carbon residue, and sulfur content (or any individual or combination of these properties). If multiple sensors 306 are used, the sensors 306 could be placed in a cluster or other grouping so that the measurements generated by the sensors 306 relate to the same general portion of crude oil. However, any suitable arrangement of sensors 306 could be used here.

With respect to density or specific gravity, weight-to-volume or volume-to-weight calculations of crude oil can be important for controlling refinery operations to achieve improved or optimal yields of finished products. Also, consistency in the density of crude oil across a given lot can be important. Specific gravity of crude oil can be expressed in various ways and is often expressed in terms of AMERICAN PETROLEUM INSTITUTE (API) gravity. Classifications of crude oil as "light" or "heavy" can be based on the crude oil's API gravity measurements. In some embodiments, the density or specific gravity of crude oil can be measured using a FORK DENSITY METER from EMERSON ELECTRIC CO., although other sensors for measuring density or specific gravity can also be used.

With respect to viscosity, viscosity is a measure of the flow properties of a material stream. In the oil and gas industry, viscosity measurements of crude oil could be carried out under specific conditions, such as at temperatures of about 100° F. (about 37.78° C.) and about 210° F. (about 98.89° C.). Viscosity can be an important property when it comes to heavy products obtained from crude oil, such as when viscosity acts as an important characterization property in blending units used to produce bunker fuel. Typically, viscosity of refinery products is specified to be within a specified range, and this can be achieved by adjusting the viscosities of the crude oil streams entering a blending unit 303. In some embodiments, the viscosity of crude oil can be measured using a FORK VISCOSITY METER from EMERSON ELECTRIC CO., although other sensors for measuring viscosity can also be used.

With respect to sulfur content, crude oil usually contains both organic and inorganic sulfur, where inorganic sulfur typically dominates the composition. As noted above, the sulfur content typically determines whether crude oil is considered sweet crude oil or sour crude oil. The sulfur content in crude oil can be responsible for numerous hydro-treating operations in a refinery process, and a typical refinery includes a number of hydro-treaters to achieve a desired separation. Inline characterization of crude oil's sulfur content can use various techniques, such as X-ray transmission, to obtain real-time measurements of sulfur content in crude oil. In some embodiments, the sulfur content of crude oil can be measured using an NEX QC benchtop energy-dispersive X-ray fluorescence (EDXRF) elemental analyzer from RIGAKU CORP., although other sensors for measuring sulfur content can also be used.

With respect to carbon residue, carbon residue for a fossil fuel relates to the tendency of that fuel to form carbon deposits at high temperatures in an inert atmosphere. In most cases, crude oil is more valuable when it has a lower carbon residue, although there are exceptions (such as when a refinery wants to produce lube oil). Various methods are known in the art for capturing carbon residue measurement, such as RCR, CCR, and MCR. Note that the determination of carbon residue may or may not occur in real-time (and may actually be performed in a laboratory setting), such as when carbon residue measurements involve measuring the amount of carbon residue left after evaporation and pyrolysis of an oil sample (which could take about 30 minutes or other extended period of time). In some embodiments, the carbon residue of crude oil can be measured using a 97400-3 MCR tester or a 12200-3 existent gum solid block bath from STANHOPE-SETA LIMITED, a K27100 or K27190 RCR tester or a K41100 MCR tester from KOEHLER INSTRUMENT CO., or an ACR-6 automated carbon residue tester or an ACR-M3 MCR tester from TANAKA SCIENTIFIC LIMITED, although other sensors for measuring carbon residue can also be used.

A crude oil property analyzer 308 receives the measurements of the crude oil properties from the one or more sensors 306. The property analyzer 308 also processes the measurements as needed, such as to filter the measurements or to consolidate the measurements (like by averaging multiple measurements of the same crude oil property in a given period of time). The property analyzer 308 further translates the original or processed sensor measurements to derive a set of process and control parameters for the distillation column 304 or other equipment. In some embodiments, the property analyzer 308 uses one or more models to translate the sensor measurements into the process and control parameters. In particular embodiments, the model or models used by the property analyzer 308 can incorporate the properties of the crude oil, the capabilities of the distillation column 304 or other equipment, and setpoints and constraints established on the distillation column 304 or other equipment (such as by owners or operators of the equipment). This can help to improve the efficiency of the distillation column 304 or other equipment since the process and control parameters are determined in line with the equipment's capabilities and limitations. In some instances, the property analyzer 308 could use EXPERION PKS technology from HONEYWELL INTERNATIONAL INC. to create the models and to apply the sensor measurements to the models in order to identify process and control parameters for the distillation column 304 or other equipment.

The property analyzer 308 includes any suitable structure configured to receive and use measurements of crude oil properties. In some embodiments, the property analyzer 308 can be implemented using the device 200 in FIG. 2. In these embodiments, the functionality of the property analyzer 308 can be implemented using instructions that are executed by the processor 202. When implemented with the industrial process control and automation system 100 of FIG. 1, the property analyzer 308 could be implemented using one or more controllers 106, operator consoles 110, servers 116, or other devices. It should be noted, however, that the property analyzer 308 can be local to or remote from the sensors 306, meaning the property analyzer 308 could reside within a control and automation system 100 or outside the control and automation system 100 (like when the property analyzer 308 is implemented in an external computing cloud or at a remote server). Note that the property analyzer 308 can also use additional data (in addition to the sensor measurements) to identify the properties of the crude oil or to translate the crude oil properties into process and control parameters. For instance, an assay data bank could identify the properties of different types or qualities of crude oil, and the property analyzer 308 could identify which type or quality of crude oil most closely matches the current sensor measurements. However, the use of the assay data bank may not be needed.

Data analytics and machine learning 310 can be used within or in conjunction with the property analyzer 308. As described above, the data analytics functions can be used to process the sensor measurements, and the machine learning functions can be used to translate the sensor measurements into the process and control parameters. The machine learning functions can also or alternatively be used to adjust the models, data analytics, or other logic used by the property analyzer 308 to identify the process and control parameters. In some embodiments, for instance, the machine learning functions can adjust the model or models used by the property analyzer 308 based on feedback, such as feedback received from the distillation column 304 (or components associated with the distillation column 304) or other equipment. The feedback can include information about operation of the distillation column 304 or other equipment or end products produced by the distillation column 304 or other equipment. Specific examples of the types of feedback that could be received include the process status of a refining process and the quality of the process outputs (end products). This may allow, for example, the machine learning functions to be used to modify the models over time so that the models identify better process and control parameters based on the crude oil parameters. The data analytics and machine learning 310 here can be implemented using any suitable structure, such as in the device 200 of FIG. 2 where instructions implementing the analytics and machine learning are executed by the processor 202. The data analytics and machine learning 310 can be implemented on the same device as the property analyzer 308 or on a different device. If implemented on different devices, the devices may or may not be local to one another.

The property analyzer 308 can provide the process and control parameters to any suitable component or components that can alter a refining or other process. For example, the property analyzer 308 could output one or more control signals that alter the overflash or other characteristics within the distillation column 304. Crude oil typically vaporizes faster than overhead and side products, and the excess vaporization is referred to as overflash. Adjusting the amount of overflash can help to improve the energy efficiency of the distillation column 304, and the property analyzer 308 can adjust the overflash based on the crude oil properties. As another example, the property analyzer 308 could output one or more control signals that alter the blending of crude oil from multiple tanks 302a-302b by the blending unit 303, such as by controlling the mixing ratio at the blending unit 303. The ability to control the mixing ratio in a crude oil blend can be useful, such as when the parameters of the distillation column 304 are predefined or manually set and cannot be altered by the property analyzer 308. Here, the mixing ratio can be controlled so that the crude oil entering the distillation column 304 has specific properties or has properties within specific ranges of values.

In some embodiments, the sensors 306 and the property analyzer 308 are generally fast enough (have adequate response times) to perform inline characterization of a moving column of crude oil. Thus, for example, at least some of the sensors 306 are able to generate sensor measurements of crude oil in the column, and the property analyzer 308 is able to process the sensor measurements and output tuned process and control parameters so that process corrections can be implemented by the time the measured portion of the crude oil column reaches certain process equipment. This allows the process equipment to be controlled much more effectively based on the properties of the crude oil that the equipment is processing.

It should be noted that, in some embodiments, the property analyzer 308 can operate in one of multiple modes of operation. For example, in an automatic mode, the property analyzer 308 could receive sensor measurements and make adjustments to process and control parameters without any user input. In a supervised mode, the property analyzer 308 could receive sensor measurements and identify adjustments to process and control parameters, but a user can determine whether the adjustments to the process and control parameters are implemented. In a manual mode, the property analyzer 308 could receive sensor measurements, and a user can manually make adjustments to process and control parameters. Of course, the property analyzer 308 could include any other or additional modes of operation, and the property analyzer 308 may or may not support all three of the identified modes of operation.

Although FIG. 3 illustrates one example of a system 300 supporting inline analysis of crude oil properties in a process control and automation system, various changes may be made to FIG. 3. For example, systems for processing crude oil can come in a variety of configurations, and FIG. 3 does not limit this disclosure to any particular configuration. Also, as noted above, not all sensors 306 may generate real-time or online sensor measurements. It is possible for at least one of the sensors 306 to generate sensor measurements in a non-real-time or offline manner, and those sensor measurements can be provided to the property analyzer 308 or other component(s) in any suitable manner. In addition, the system 300 here can include any suitable number of each of the components 302a-310. For instance, the same property analyzer 308 could be used with one or more sets of sensors 306 or one or more distillation columns 304, or multiple property analyzers 308 could be used with different distillation columns 304.

Figure 4:
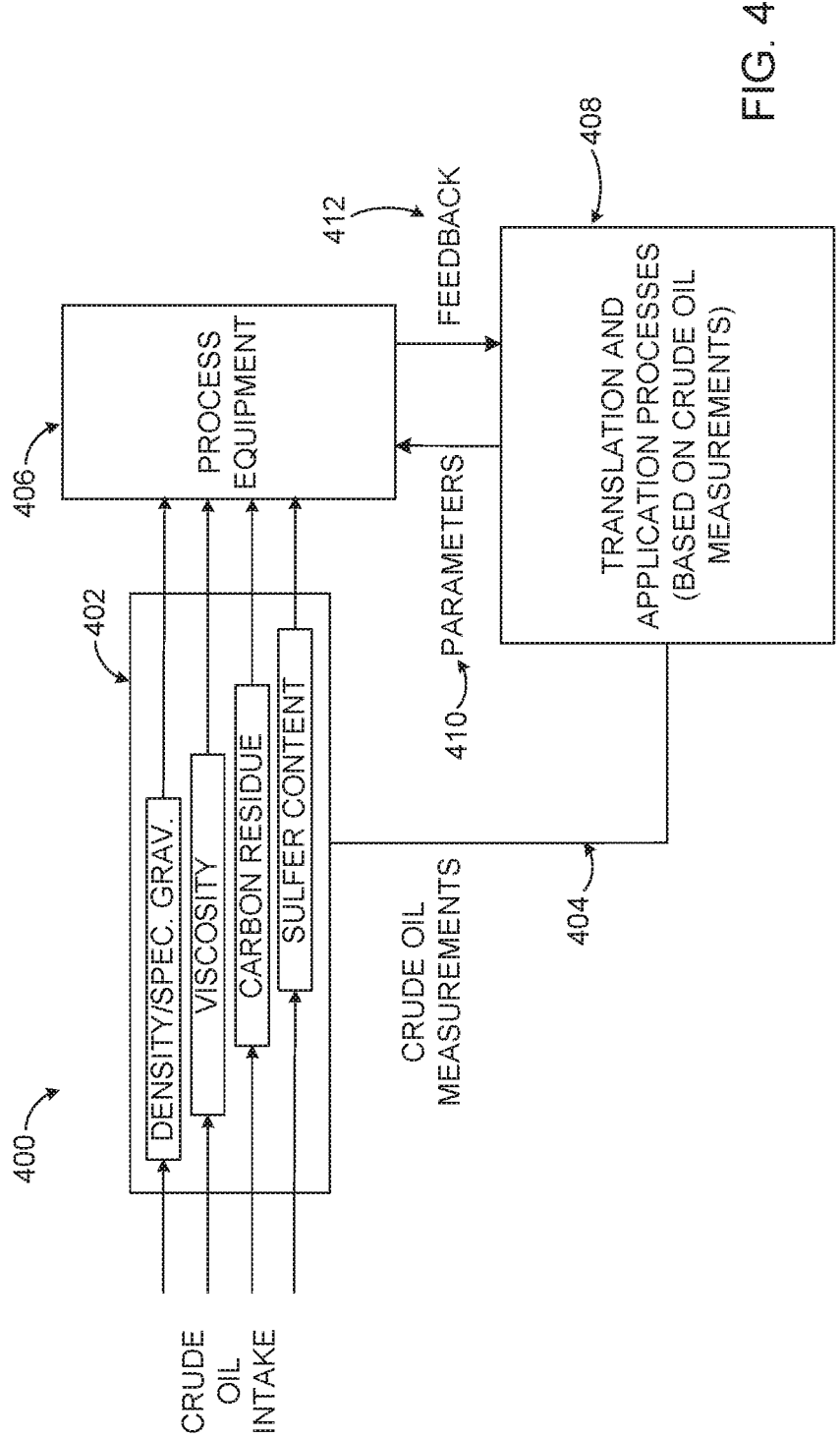
FIG. 4 illustrates an example process supporting crude oil analysis in a process control and automation system according to this disclosure.

FIG. 4 illustrates an example process 400 supporting crude oil analysis in a process control and automation system according to this disclosure. The process 400 could, for example, be performed using the system 300 of FIG. 3, which can operate using one or more devices 200 of FIG. 2 in the system 100 of FIG. 1. However, the process 400 could be performed using any suitable device(s) and in any suitable system.

As shown in FIG. 4, a cluster 402 of sensors (such as the sensors 102a-102b, 306) captures crude oil measurements 404 of incoming crude oil. The crude oil measurements 404 measure any suitable property or properties of the crude oil, such as density or specific gravity, viscosity, carbon residue, and sulfur content (or any one or combination thereof). In some embodiments, the crude oil being measured here represents a moving column of crude oil, which can pass through or near the cluster 402 of sensors. As noted above, one or more sensors can measure one or more parameters of the crude oil with sufficient accuracy and speed. The crude oil is being provided to process equipment 406, which can receive or process the crude oil in some manner. For instance, the process equipment 406 could represent a tank, blending unit, or crude oil distillation column and its associated controllers.

The crude oil measurements 404 are provided to translation and application processes 408. These processes 408 can be executed by at least one processing device, such as a device 200 that implements the crude oil property analyzer 308. The translation and application processes 408 can gather the crude oil measurements 404 and perform filtering and consolidation of the crude oil measurements 404. The translation and application processes 408 can also perform data analytics based on process optimization algorithms by applying the crude oil measurements 404 to one or more pre-stored models or other models. The translation and application processes 408 can thereby derive a set of process and control parameters 410 for the process equipment 406 based on the crude oil measurements 404. Deriving the process and control parameters 410 for the specific crude oil being measured can be inline, and the parameters 410 can be applied to the ongoing process. The derived parameters 410 are therefore sent to the process equipment 406 in order to adjust operation of the process equipment 406.

Optionally, feedback 412 can be sent from the process equipment 406 or related equipment to the translation and application processes 408. As noted above, the feedback 412 can be used by the translation and application processes 408 to improve the models, data analytics, or other operations performed by the translation and application processes 408.

In this way, one or more algorithms can be executed based on the crude oil properties that are sensed, and models (which can optionally indicate process equipment capabilities, setpoints, and constraints) can be used to ensure the best efficiency is obtained. This can be particularly advantageous in refineries or other processes where crude oil feeds are changed frequently and process corrections are made to process equipment 406 in order to account for the different properties of the crude oil.

Although FIG. 4 illustrates one example of a process 400 supporting crude oil analysis in a process control and automation system, various changes may be made to FIG. 4. For example, FIG. 4 does not limit this disclosure to any particular configuration of equipment. Also, the communication paths for data in FIG. 4 are for illustration only. Any suitable mechanisms can be used to transfer data between components or functions in FIG. 4, and those mechanisms can include any desired features (such as encryption or quality of service).

Figure 5:
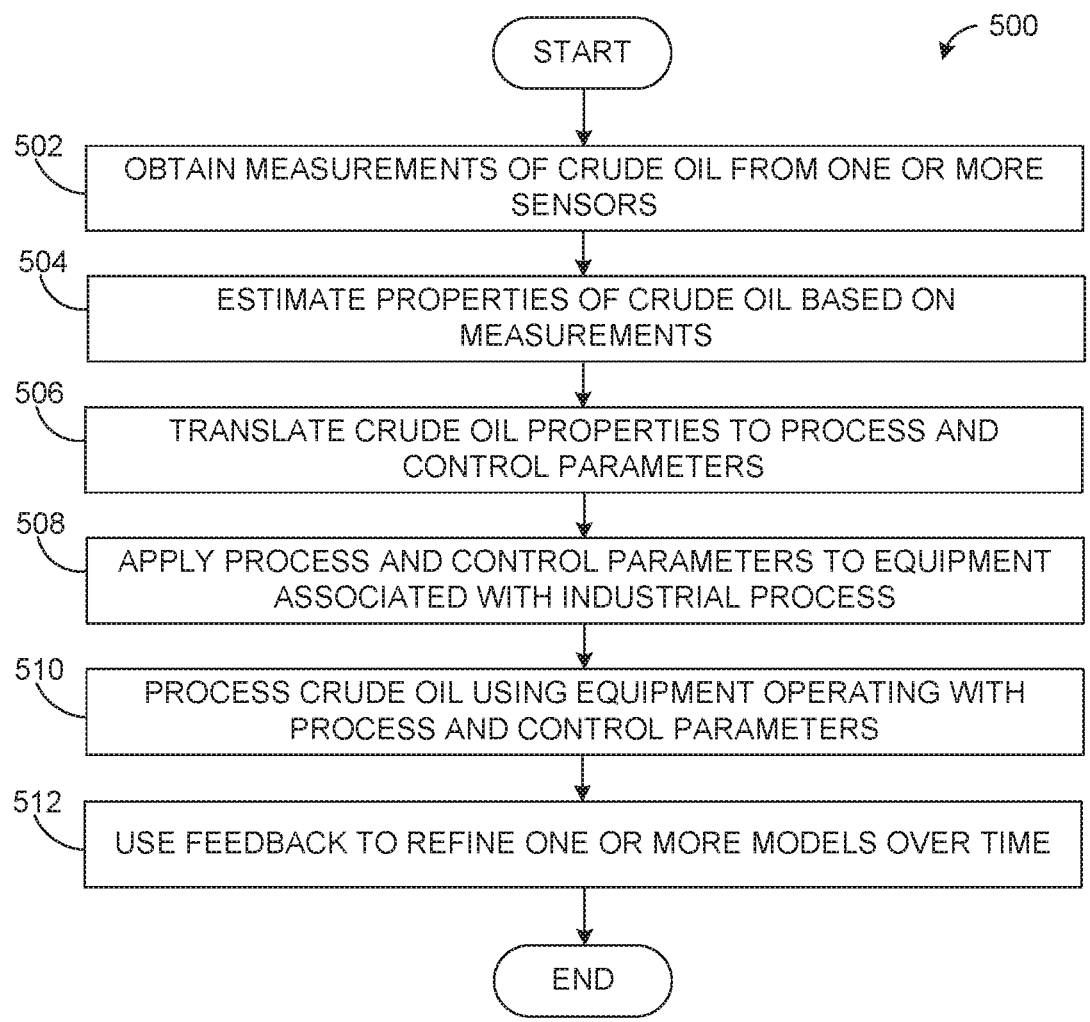
FIG. 5 illustrates an example method for optimizing crude oil distillation or other processes by inline analysis of crude oil properties according to this disclosure.

FIG. 5 illustrates an example method 500 for optimizing crude oil distillation or other processes by inline analysis of crude oil properties according to this disclosure. The method 500 could, for example, be performed using the system 300 of FIG. 3, which can be used in the process 400 of FIG. 4 and operate using one or more devices 200 of FIG. 2 in the system 100 of FIG. 1. However, the method 500 could be performed using any suitable device(s) and in any suitable system and support any suitable process for inline analysis of crude oil properties.

As shown in FIG. 5, measurements of crude oil are obtained from one or more sensors at step 502. This can include, for example, a processor 202 in a device 200 operating as the crude oil property analyzer 308 receiving measurements from one or more sensors 102a-102b, 306. The processor 202 can receive any suitable measurements associated with the crude oil, such as density or specific gravity, viscosity, carbon residue, or sulfur content (or any combination thereof). A subset of the measurements that are received could optionally represent offline or laboratory measurements, meaning the measurements are not captured in real-time by an inline sensor. However, at least some of the measurements that are received are from at least one inline sensor. One or more properties of the crude oil can be estimated using the measurements at step 504. This can include, for example, the processor 202 filtering and consolidating the measurements for each crude oil property being examined. Note, however, that the sensor measurements could also be used as the one or more crude oil properties without further processing.

The one or more crude oil properties are translated into a set of process and control parameters at step 506. This can include, for example, the processor 202 using one or more models to identify process and control parameters based on the crude oil properties. As noted above, the model(s) can associate values of the crude oil properties and the values of the process and control parameters. The process and control parameters are applied to equipment associated with an industrial process at step 508. This can include, for example, the processor 202 transmitting the process and control parameters 410 to the process equipment 406. The process and control parameters 410 are implemented by the process equipment 406 in order to alter how the process equipment 406 operates. For instance, the process equipment 406 could represent at least one controller 106 that uses the process and control parameters 410 in calculations during control intervals.

The crude oil is processed using the equipment operating with the process and control parameters at step 510. This can include, for example, a controller 106 causing the blending unit 303 to mix crude oil from different tanks 302a-302b in a specific manner (such as a specific mixing ratio) in accordance with the process and control parameters 410. This can also include one or more controllers 106 causing the crude oil distillation column 304 to perform refining operations in accordance with the process and control parameters 410. Ideally, the process and control parameters 410 are tuned in order to increase or optimize the processing of the crude oil by the equipment. Steps 502-510 can occur repeatedly in order to adjust the overall process so that the process equipment is efficiently processing the crude oil over time. For instance, steps 502-510 can occur repeatedly to account for one or more crude oil feed changes in which the quality or type of crude oil changes, such as from initially-used crude oil to newly-injected crude oil.

At some point, feedback can be used to refine one or more models over time at step 512. This can include, for example, the processor 202 receiving feedback, such as process status or quality of process outputs, from the process equipment 406 or other equipment. This can also include the processor 202 applying data analytics and machine learning 310 to determine how one or more models might be changed in order to improve the process status or quality of process outputs. The processor 202 could perform various actions here, such as modifying a model and seeing if it results in improvements to the process status or quality of process outputs. If not, the processor 202 could undo the changes or make other changes and identifying any improvements to the process status or quality of process outputs. The changed model(s) can be used during subsequent iterations though step 506.

Although FIG. 5 illustrates one example of a method 500 for optimizing crude oil distillation or other processes by inline analysis of crude oil properties, various changes may be made to FIG. 5. For example, while shown as a series of steps, various steps in FIG. 5 could overlap, occur in parallel, occur in a different order, or occur any number of times.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
  obtaining inline measurements via a sensor of one or more properties of crude oil;
  translating the measurements into a set of process and control parameters; and
  applying the process and control parameters to process equipment, the process and control parameters configuring the process equipment to process the crude oil having the one or more properties,
  wherein the one or more properties of the crude oil that are obtained with the sensor comprise at least one of: density, specific gravity, viscosity, carbon residue, and sulfur content of the crude oil.

2. The method of claim 1, wherein obtaining the inline measurements comprises at least one of:
  obtaining the inline measurements when the crude oil is stored in at least one tank;
  obtaining the inline measurements when the crude oil is being transported through at least one pipe; and
  obtaining the inline measurements when the crude oil is entering or within a crude oil distillation column.

3. The method of claim 1, wherein applying the process and control parameters to the process equipment comprises at least one of:
  applying the process and control parameters to one or more controllers associated with a blending unit in a refinery; and
  applying the process and control parameters to one or more controllers associated with a crude oil distillation column in the refinery.

4. The method of claim 1, wherein:
  translating the measurements into the set of process and control parameters comprises using one or more models; and
  the method further comprises updating the one or more models through machine learning and using feedback associated with the process equipment.

5. The method of claim 1, wherein:
  translating the measurements into the set of process and control parameters comprises determining a mixing ratio; and
  applying the process and control parameters to the process equipment comprises causing a blending unit to mix multiple crude oil streams at the determined mixing ratio.

6. The method of claim 1, further comprising:
  receiving offline measurements of one or more additional properties of the crude oil;
  wherein translating the measurements comprises translating the inline and offline measurements into the set of process and control parameters.

7. An apparatus comprising:
  at least one processor configured to:
    obtain inline measurements via a sensor of one or more properties of crude oil;
    translate the measurements into a set of process and control parameters; and
    apply the process and control parameters to process equipment, the process and control parameters configuring the process equipment to process the crude oil having the one or more properties,
  wherein the one or more properties of the crude oil that are obtained with the sensor comprise at least one of: density, specific gravity, viscosity, carbon residue, and sulfur content of the crude oil.

8. The apparatus of claim 7, wherein, to obtain the inline measurements, the at least one processor is configured to at least one of:
  obtain the inline measurements when the crude oil is stored in at least one tank;
  obtain the inline measurements when the crude oil is being transported through at least one pipe; and
  obtain the inline measurements when the crude oil is entering or within a crude oil distillation column.

9. The apparatus of claim 7, wherein, to apply the process and control parameters to the process equipment, the at least one processor is configured to at least one of:
  apply the process and control parameters to one or more controllers associated with a blending unit in a refinery; and
  apply the process and control parameters to one or more controllers associated with a crude oil distillation column in the refinery.

10. The apparatus of claim 7, wherein:
  to translate the measurements into the set of process and control parameters, the at least one processor is configured to use one or more models; and
  the at least one processor is further configured to update the one or more models through machine learning and using feedback associated with the process equipment.

11. The apparatus of claim 7, wherein:
  to translate the measurements into the set of process and control parameters, the at least one processor is configured to determine a mixing ratio; and
  to apply the process and control parameters to the process equipment, the at least one processor is configured to cause a blending unit to mix multiple crude oil streams at the determined mixing ratio.

12. The apparatus of claim 7, wherein:
  at least one processor is further configured to receive offline measurements of one or more additional properties of the crude oil; and
  the at least one processor is configured to translate the inline and offline measurements into the set of process and control parameters.

13. A non-transitory computer readable medium containing instructions that, when executed, cause at least one processing device to:
  obtain inline measurements via a sensor of one or more properties of crude oil;
  translate the measurements into a set of process and control parameters; and
  apply the process and control parameters to process equipment, the process and control parameters configuring the process equipment to process the crude oil having the one or more properties,
  wherein the one or more properties of the crude oil that are obtained with the sensor comprise at least one of: density, specific gravity, viscosity, carbon residue, and sulfur content of the crude oil.

14. The non-transitory computer readable medium of claim 13, wherein the instructions that when executed cause the at least one processing device to obtain the inline measurements comprise at least one of:
  instructions that when executed cause the at least one processing device to obtain the inline measurements when the crude oil is stored in at least one tank;
  instructions that when executed cause the at least one processing device to obtain the inline measurements when the crude oil is being transported through at least one pipe; and
  instructions that when executed cause the at least one processing device to obtain the inline measurements when the crude oil is entering or within a crude oil distillation column.

15. The non-transitory computer readable medium of claim 13, wherein the instructions that when executed cause the at least one processing device to apply the process and control parameters to the process equipment comprise at least one of:
  instructions that when executed cause the at least one processing device to apply the process and control parameters to one or more controllers associated with a blending unit in a refinery; and
  instructions that when executed cause the at least one processing device to apply the process and control parameters to one or more controllers associated with a crude oil distillation column in the refinery.

16. The non-transitory computer readable medium of claim 13, wherein:
the instructions that when executed cause the at least one processing device to translate the measurements into the set of process and control parameters comprise:
instructions that when executed cause the at least one processing device to translate the measurements into the set of process and control parameters using one or more models; and
the medium further contains instructions that when executed cause the at least one processing device to update the one or more models through machine learning and using feedback associated with the process equipment.

17. The non-transitory computer readable medium of claim 13, wherein:
the instructions that when executed cause the at least one processing device to translate the measurements into the set of process and control parameters comprise:
instructions that when executed cause the at least one processing device to determine a mixing ratio; and
the instructions that when executed cause the at least one processing device to apply the process and control parameters to the process equipment comprise:
instructions that when executed cause the at least one processing device to cause a blending unit to mix multiple crude oil streams at the determined mixing ratio.

* * * * *